(12) United States Patent
Lee

(10) Patent No.: US 9,012,426 B2
(45) Date of Patent: Apr. 21, 2015

(54) PHARMACEUTICAL ANTI-ANGIOGENIC COMPOSITION INCLUDING A MICRORNA-382 INHIBITOR

(75) Inventor: You Mie Lee, Suseong-gu (KR)

(73) Assignee: Kyungpook National University Industry—Academic Cooperation Foundation (KR)

( * ) Notice: Subject to any disclaimer, the term of this patent is extended or adjusted under 35 U.S.C. 154(b) by 0 days.

(21) Appl. No.: 14/240,539

(22) PCT Filed: Aug. 29, 2012

(86) PCT No.: PCT/KR2012/006910
§ 371 (c)(1),
(2), (4) Date: Feb. 24, 2014

(87) PCT Pub. No.: WO2013/032231
PCT Pub. Date: Mar. 7, 2013

(65) Prior Publication Data
US 2014/0227246 A1    Aug. 14, 2014

(30) Foreign Application Priority Data

Aug. 30, 2011 (KR) .................. 10-2011-0086987
Aug. 29, 2012 (KR) .................. 10-2012-0094794

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ........ *C12N 15/113* (2013.01); *C12N 2310/113* (2013.01)

(58) Field of Classification Search
USPC .......................................... 536/24.5; 514/44
See application file for complete search history.

(56) References Cited

U.S. PATENT DOCUMENTS

2011/0184043 A1    7/2011    Lagos-quintana et al.

FOREIGN PATENT DOCUMENTS

| KR | 10-2010-0009268 | 1/2010 |
| WO | 2008/014008 | 1/2008 |

OTHER PUBLICATIONS

Kriegel et al. (Nucleic Acids Research, vol. 38, No. 22, published online Aug. 16, 2010, pp. 8338-8347).*
Kim et al., "The roles of microRNA-382 induced by hypoxia in angiogenesis," 2010, Master thesis, Kyunkpook National University Graduate School.

* cited by examiner

*Primary Examiner* — Terra Cotta Gibbs
(74) *Attorney, Agent, or Firm* — Riverside Law LLP

(57) ABSTRACT

The present invention relates to an anti-angiogenic composition, and more particularly, to a pharmaceutical anti-angiogenic composition including a microRNA-382 inhibitor. The inventors of the present invention have confirmed that microRNA-382, the expression of which is elevated in stomach cancer cells in a low oxygen environment, affects the promotion of angiogenesis induced in a low oxygen environment. Therefore, the pharmaceutical composition of the present invention inhibits microRNA-382 and thus inhibits angiogenesis and cell proliferation, and is expected ultimately to be valuably used in the treatment of cancer.

1 Claim, 15 Drawing Sheets

Fig. 10

| | |
|---|---|
| 3' gcuuAGGUGGU-GCUUGUUGAAg 5' hsa-miR-382 | (SEQ ID NO: 1) |
|       |||:||:||||||| | |
| 956:5' uaccUACAUCAGUCAACAACUUa 3' PTEN | (SEQ ID NO: 2) |

```
     .960........970........980.........
Hsa --UAC-CUACAUCAGUCAACAACUU-ACAC-UU   (SEQ ID NO: 3)
Mm. --UAC-CUACAUCAGUCAACAACUU-ACA--U    (SEQ ID NO: 4)
Rno --UCC-CUACAUCAGUCAACAACUU-ACAU-UU   (SEQ ID NO: 5)
Cn  --UAC-CUACAUCAGUCAACAACUU-ACAC---   (SEQ ID NO: 6)
Bta --UAC-CUACAUCAGUCAACAACUU-ACAC-UU   (SEQ ID NO: 7)
Laf --UAC-CUACAUCAGUCAACAACUU-ACAC---   (SEQ ID NO: 8)
Con ..UAC.CUACAUCAGUCAACAACUU.ACAC.U.   (SEQ ID NO: 9)
```

PHARMACEUTICAL ANTI-ANGIOGENIC COMPOSITION INCLUDING A MICRORNA-382 INHIBITOR

STATEMENT REGARDING GOVERNMENT RIGHTS

This invention was made with government support of the Republic of Korea under Contract Nos. 1220130, NRF-2012R1A1A2007369, and NRF-2012R1A4A1028835 awarded by the Korean Ministry of Health and Welfare, Ministry of Education, Science and Technology, and Korean Ministry of Science, ICT and Future Planning, respectively. The government has certain rights in the invention.

CROSS-REFERENCE TO RELATED APPLICATIONS

This application is the U.S. national phase application filed under 35 U.S.C. §371 claiming benefit to International Patent Application No. PCT/KR2012/006910, filed on Aug. 29, 2012, which is entitled to priority under 35 U.S.C. §119(a)-(d) to Korea application nos. 10-2011-0086987, filed Aug. 30, 2011 and 10-2012-0094794, filed Aug. 29, 2012, each of which application is hereby incorporated herein by reference in its entirety.

TECHNICAL FIELD

The present invention relates to a composition for inhibiting angiogenesis, more particularly to a pharmaceutical composition for inhibiting angiogenesis, including a microRNA-382 inhibitor.

BACKGROUND ART

Cancer is a leading cause of death worldwide, outnumbering deaths from cardiovascular diseases and cerebrovascular diseases. An attack rate of cancer has increased in accordance with economic growth and changes of disease forms caused by changes in lifestyle and dietary patterns, causing about 7.6 million deaths from cancer and 12.66 million new cases of cancer to appear in 2008, which demonstrates the continuous increase in cancer occurrence and deaths from cancer. In accordance with societal developments, populations continue to become older, and therefore the burden of cancer occurrence is predicted to increase more. Also, while an attack rate of cancer has also gradually increased among young people due to genetic causes and stress, and thus the prevention and treatment of cancer is more important than ever before, innovative treatments for cancer, such as development of anti-cancer agents having superior effects without side effects, have not been available, and therefore development of such treatments is strongly desired in the art.

Among such treatments, a method by which proliferation of tumors and cancer cells can be inhibited by limiting a supply of oxygen and nutrients is known, and efforts to develop technology related thereto are active. For this purpose, expression of factors among genes of tumors and cancer cells expressed under a hypoxia condition that are involved in glucose metabolism and generation of new blood vessels, and their mechanisms of adapting to a surrounding micro-environment are important in understanding growth and proliferation of tumors and cancer cells.

On the other hand, microRNA is small non-coding RNA which inhibits gene expression at a control step after transcription. MicroRNA is composed of 18 to 25 nucleotides on average and forms a hairpin structure. It complementarily binds to a 3'-UTR portion of the sequence of a target gene to inhibit mRNA from decomposing or translating to a protein, and it has been known that at least about 5000 human genes are targets of microRNA. Functions of microRNA in vivo can be various, and for instance, include cell differentiation and proliferation, control of developmental stages and metabolism, angiogenesis, and apoptosis, depending on what type of target gene is eventually controlled. As such, importance of the functions of microRNA is increasing, and accordingly, related research is becoming more active.

An appearance of expression of modified microRNA has been reported in various cancers, and its involvement in controlling cancer-stimulating genes or cancer-inhibiting genes is being discovered. In addition, it was proved that microRNA controls a step of forming new blood vessels, and a possibility of developing a novel treatment method for inhibiting blood vessel diseases and cancer using such mechanism is suggested. What is desperately required is the development of a drug for preventing cancer in an early stage of cancer cell formation and for treating cancer by inhibiting angiogenesis induced in cancer through the mechanism of controlling expression of cancer-related genes of microRNA.

DISCLOSURE

Technical Problem

Accordingly, the present inventors have sought to discover, via extensive studies, particular microRNA which is involved in angiogenesis under a hypoxia environment without causing any side effects and to use the same in a composition for effectively treating cancer, and as a result, have discovered the inhibition effect for angiogenesis when microRNA-382, expression of which is increased in gastric cancer cells, is inhibited, and thereby accomplished the present invention.

Therefore, an aim of the present invention is to provide a pharmaceutical composition for inhibiting angiogenesis around cancer through inhibition of microRNA-382, expression of which is increased under a hypoxia environment, and a method for inhibiting angiogenesis using the pharmaceutical composition.

However, the problem to be solved by the present invention is not limited to that indicated above, and other problems which are not described herein would be clearly understood by those skilled in the art via the following description.

Technical Solution

One aspect of the present invention provides a pharmaceutical composition for inhibiting angiogenesis, including a microRNA-382 inhibitor. The pharmaceutical composition for inhibiting angiogenesis is characterized by being used for treatment of cancer by inhibiting proliferation of cancer cells. The cancer cells include gastric cancer cells.

Another aspect of the present invention provides a method for inhibiting angiogenesis, including a step of administering a pharmaceutically effective amount of the pharmaceutical composition to an individual.

Advantageous Effects

The pharmaceutical composition of the present invention can inhibit angiogenesis and proliferation of cancer cells by inhibiting microRNA-382, and therefore is expected to be eventually useful in treatment of cancer.

DESCRIPTION OF DRAWINGS

FIG. 10 illustrates an image showing a binding site of 3'-UTR of PTEN with microRNA-382, as well as SEQ ID NOs 1-9.

BEST MODES OF THE INVENTION

The present invention provides a pharmaceutical composition for inhibiting angiogenesis, including a microRNA-382 inhibitor. The present inventors confirmed a control action of microRNA-382 for angiogenesis and proliferation of blood vessel endothelial cells under a hypoxia environment through experiments. In addition, it was confirmed through experiments that expression of microRNA-382 is increased in gastric cancer cells under a hypoxia condition, and that proliferation performance, migration performance, and performance of forming blood vessels of surrounding blood vessel endothelial cells are decreased when microRNA-382 is inhibited using an inhibitor.

On the other hand, the present inventors confirmed different expression of microRNA in a normal oxygen state and a hypoxia state of cancer cells, and in particular that expression of microRNA-382 is increased in the hypoxia state. This suggests that microRNA-382 is involved in proliferation of cancer cells, and therefore can be a target of cancer treatment.

Accordingly, the present invention provides a pharmaceutical composition which inhibits microRNA-382 in order to inhibit angiogenesis and proliferation of blood vessel endothelial cells around cancer, and which is to be used for treatment of cancer. The cancer includes gastric cancer.

Figure 1:
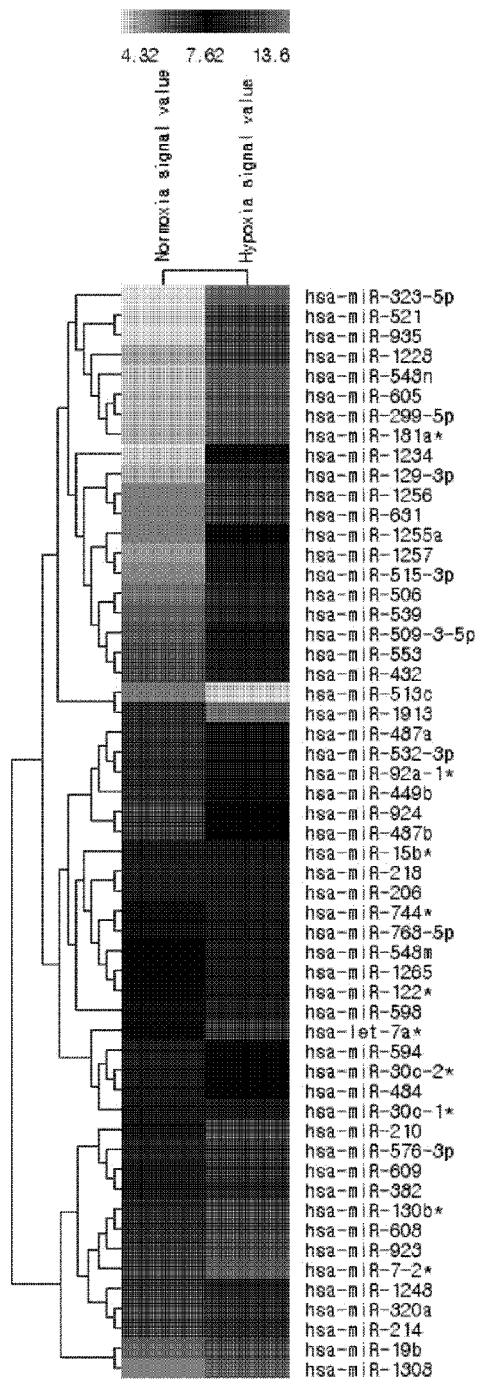
FIG. 1 illustrates results showing an appearance of the expression of microRNA through microarray experiments when MKN1 cells, which are a gastric cancer cell strain, were cultivated under a hypoxia condition compared with those under a normal oxygen condition. Under the two conditions, the change was observed in the expression amount of many types of microRNA, and among them, the expression of microRNA-382 was increased under the hypoxia condition.
Figure 2:
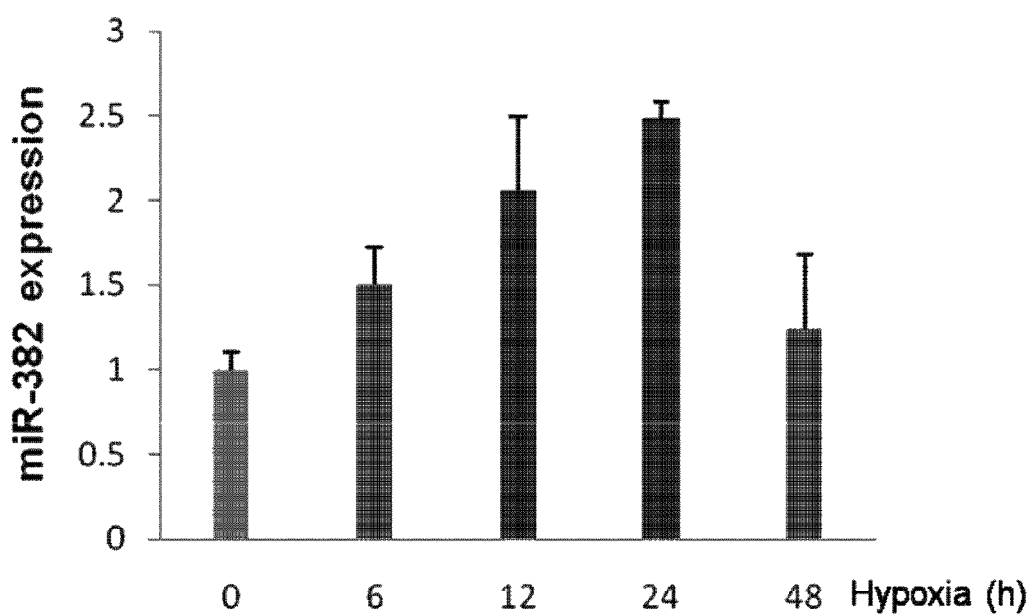
FIG. 2 illustrates the expression amount of microRNA-382 through a real-time PCR experiment in which MKN1 cells, which are a gastric cancer cell strain, were cultivated in accordance with time under the hypoxia condition. It was confirmed that the expression of microRNA-382 is increased under the hypoxia condition compared with that under the normal oxygen condition, and the maximum expression of microRNA-382 was found at a cultivation time of 24 hours.

In one embodiment of the present invention, microRNA showing different expression amounts when MKN1 cells, which are a gastric cancer cell strain, are under the hypoxia condition was confirmed through microarray experiments (refer to FIG. 1), and in addition, it was confirmed through real-time PCR that, among them, microRNA-382 shows the highest expression at 24 hours under the hypoxia condition (refer to FIG. 2).

Further, in another embodiment of the present invention, the expression of microRNA-382, expression of which is increased in gastric cancer cells in the hypoxia state, was decreased using an inhibitor. Decreased cell proliferation performance was confirmed when blood vessel endothelial cells were cultivated in the conditioned medium which was extracted after 6 hours, 12 hours, and 24 hours (refer to FIG. 3), and also confirmed were decreased migration performance and decreased performance of forming blood vessels of the blood vessel endothelial cells which were cultivated in this conditioned medium (refer to FIG. 4 and FIG. 5).

Figure 6:
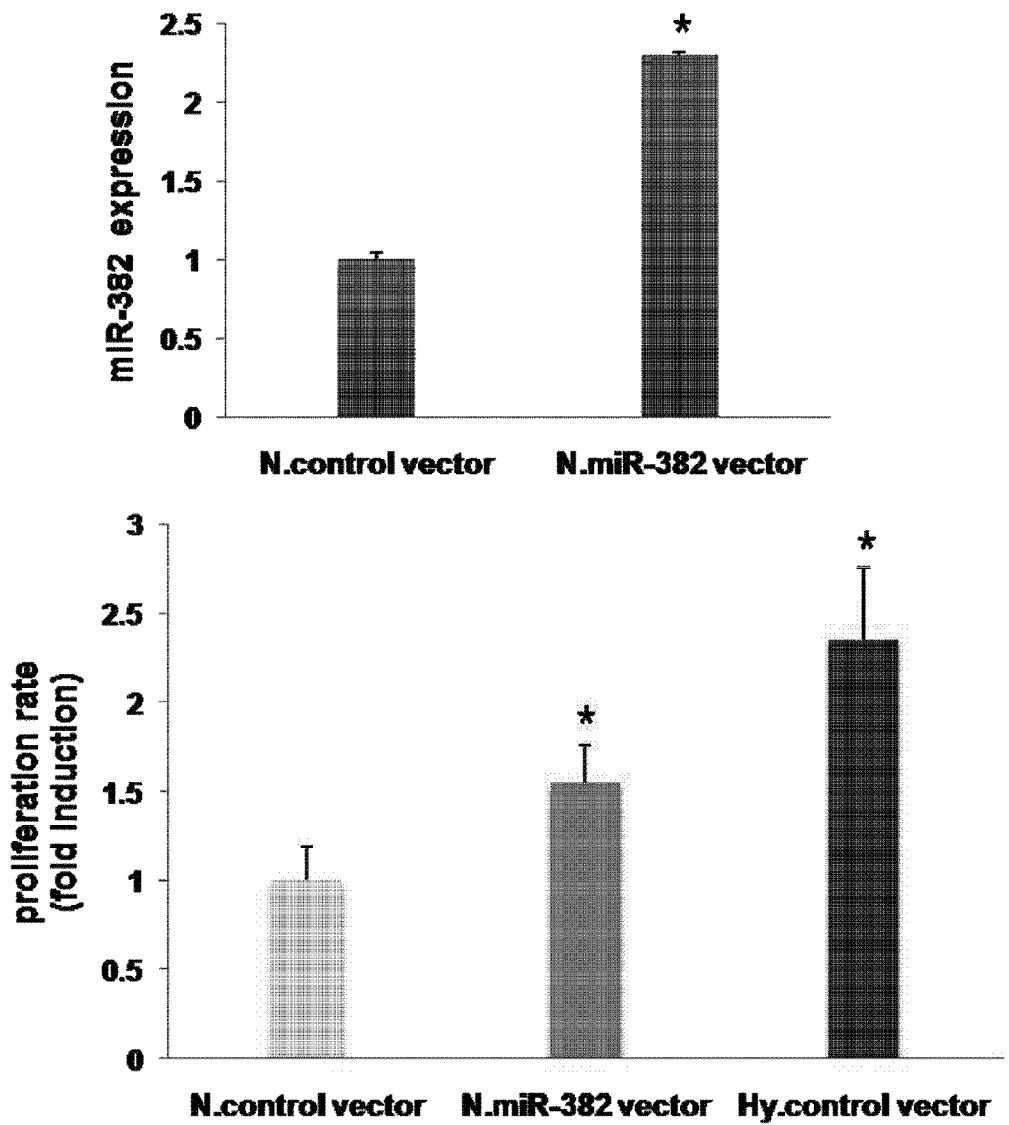
FIG. 6 illustrates results of increased proliferation performance of the cells when blood vessel endothelial cells were cultivated in the conditioned medium in which the expression of microRNA-382 was increased under the normal oxygen condition.
Figure 7:
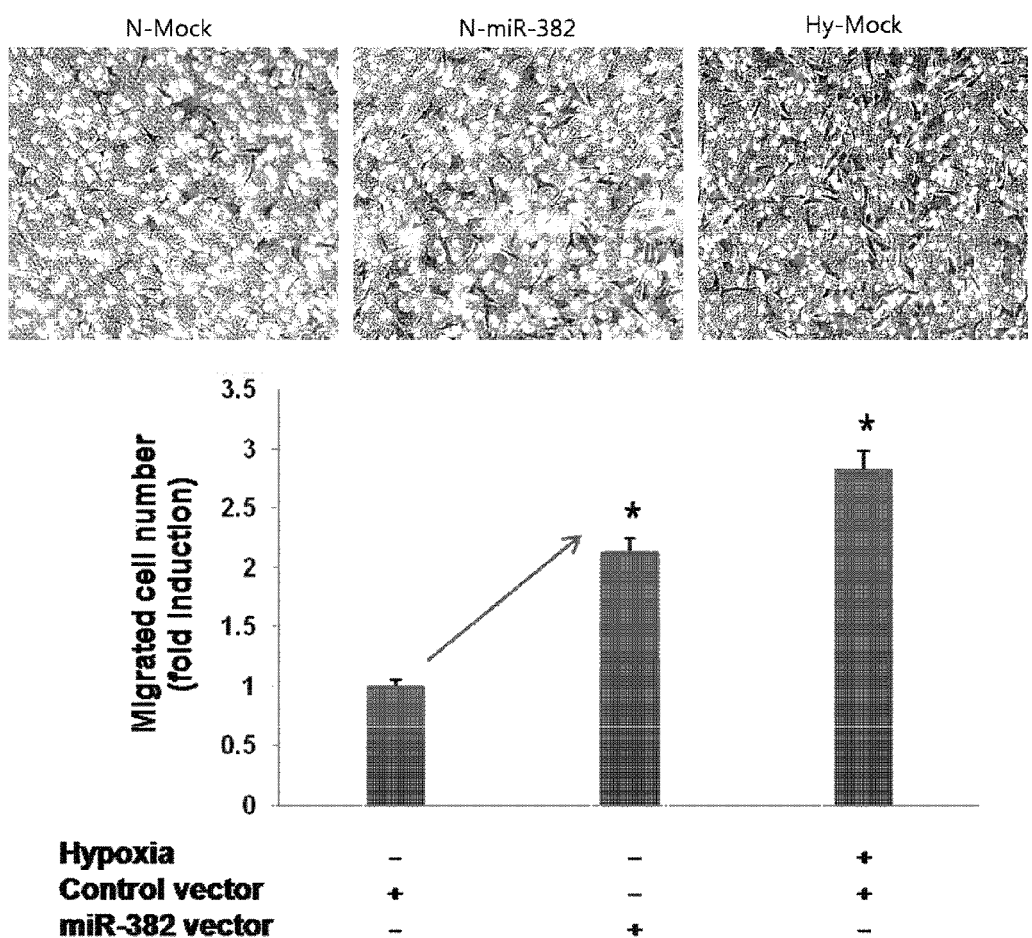
FIG. 7 illustrates results of increased migration performance of the cells when blood vessel endothelial cells were cultivated in the conditioned medium in which the expression of microRNA-382 was increased under the normal oxygen condition.
Figure 8:
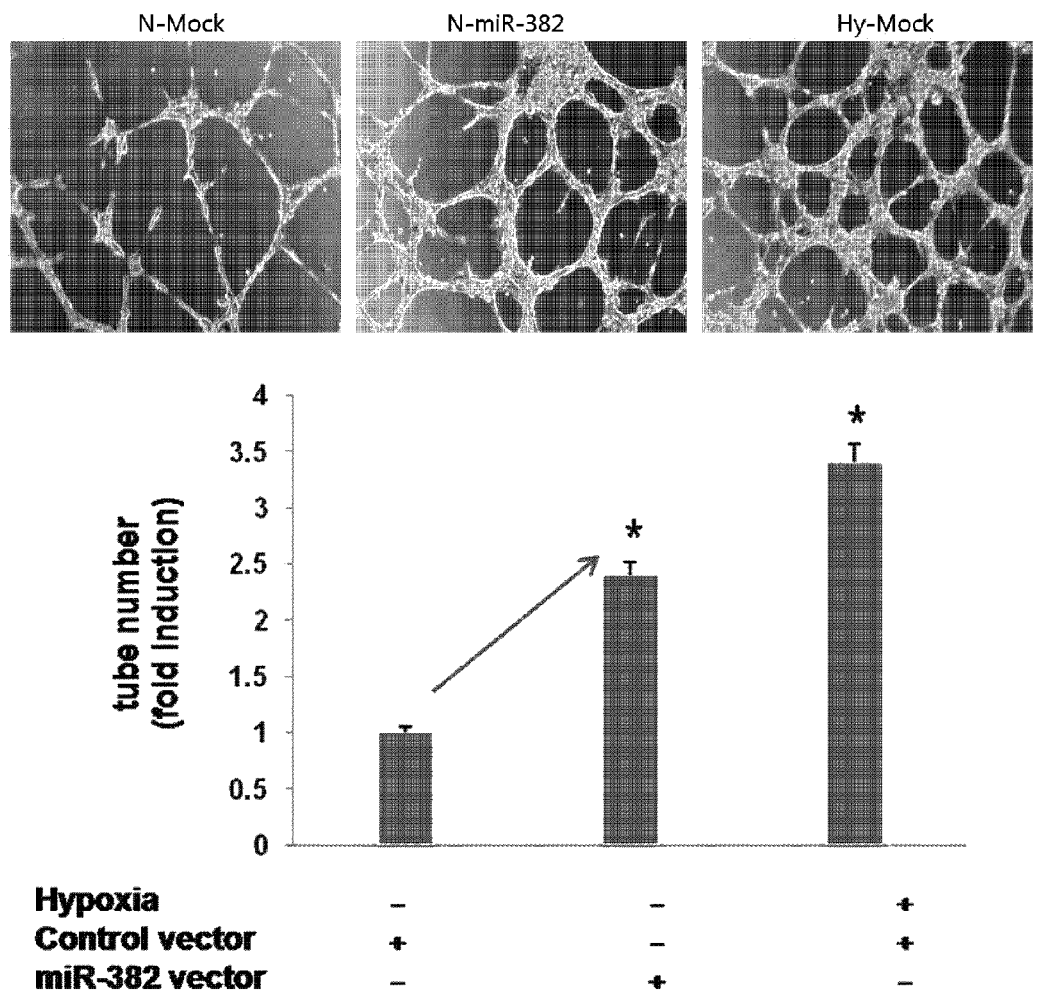
FIG. 8 illustrates results of increased performance of forming blood vessels of the cells when blood vessel endothelial cells were cultivated in the conditioned medium in which the expression of microRNA-382 was increased under the normal oxygen condition.

Furthermore, increased cell proliferation performance was confirmed when blood vessel endothelial cells were cultivated in the conditioned medium which was extracted after over-expressing microRNA-382 in gastric cancer cells in the normal oxygen state (refer to FIG. 6), and also confirmed were similarly increased migration performance and performance of forming blood vessels of the blood vessel endothelial cells (refer to FIG. 7 and FIG. 8).

Figure 12:
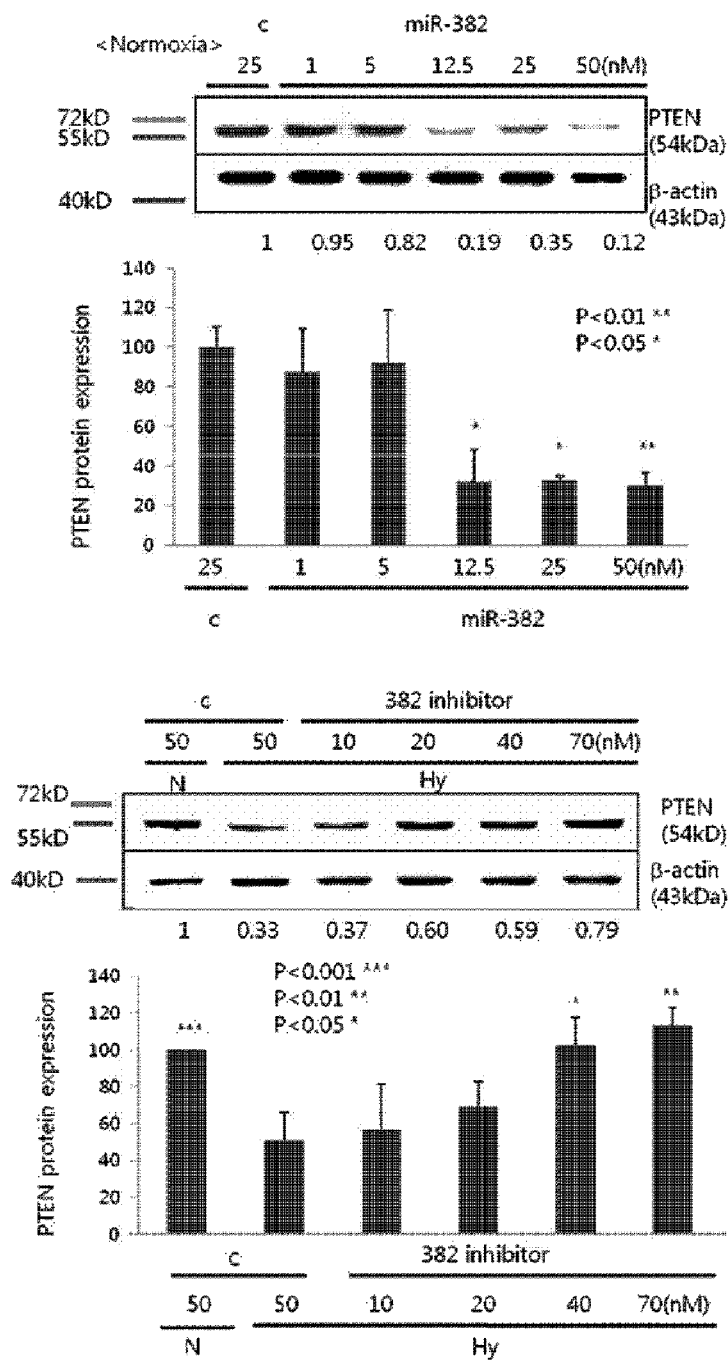
FIG. 12 illustrates results of confirming a change of an expression amount of PTEN protein by microRNA-382.
Figure 13:
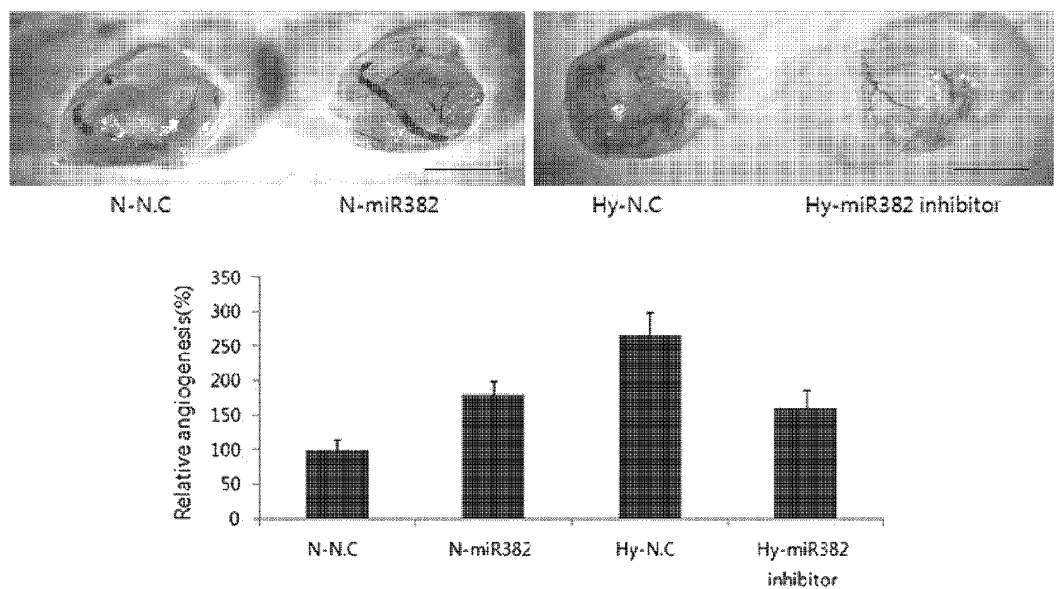
FIG. 13 illustrates results of conducting a CAM assay to confirm an effect of microRNA-382 in accelerating angiogenesis (scale bar=2 mm)
Figure 14:
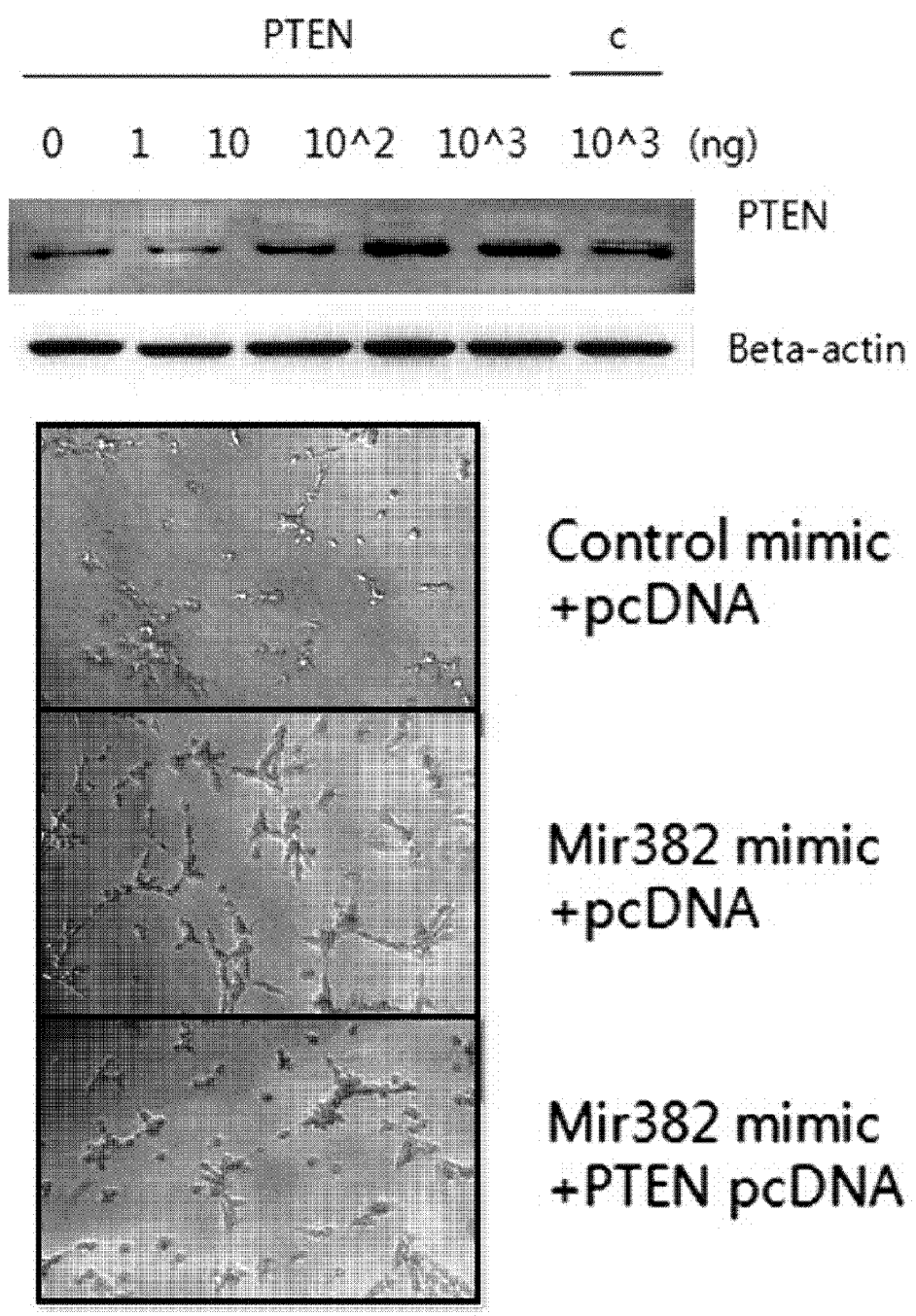
FIG. 14 illustrates results of conducting a tube formation assay to confirm inhibition by PTEN on the effect of microRNA-382 in accelerating angiogenesis.
Figure 15:
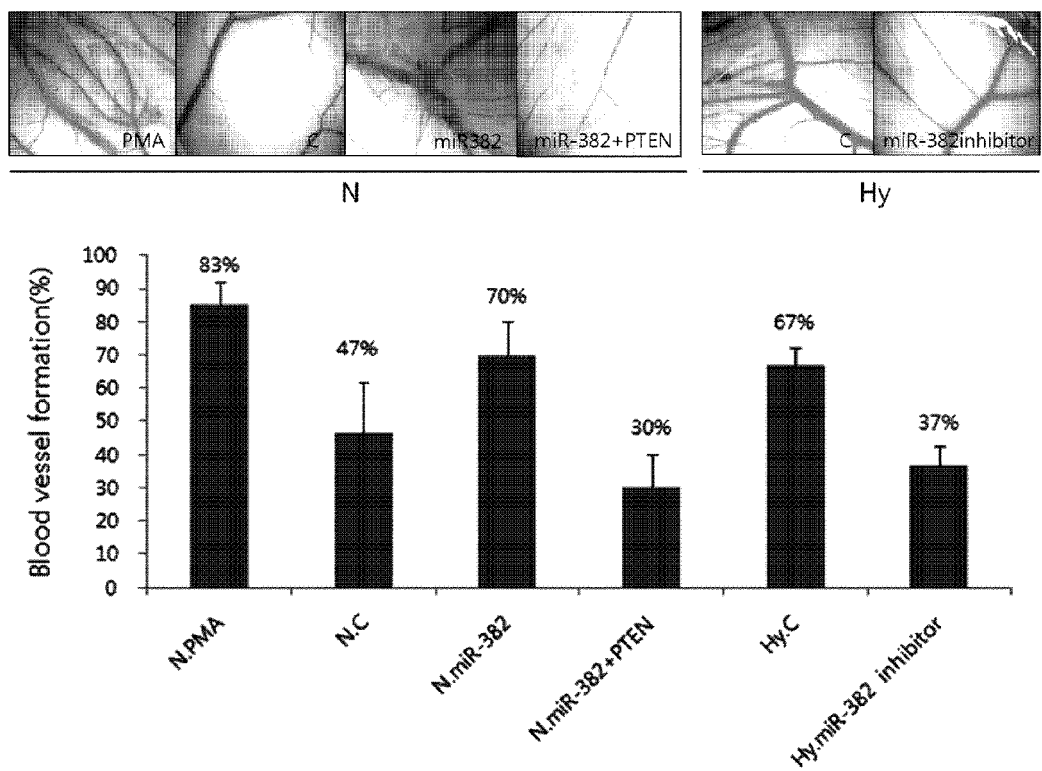
FIG. 15 illustrates results of conducting a CAM assay to confirm inhibition by PTEN on the effect of microRNA-382 in accelerating angiogenesis.

In addition, it was confirmed that a target gene of microRNA-382 is PTEN, and that microRNA-382 binds to 3'-UTR of PTEN (refer to FIG. 9 to FIG. 12), and the effect of microRNA-382 in accelerating angiogenesis in vivo was also confirmed via a CAM assay and a tube formation assay (refer to FIG. 13 to FIG. 15).

From the above, the present inventors confirmed that microRNA-382 functions to accelerate angiogenesis and proliferation of blood vessel endothelial cells. Ultimately, the above results suggest that metastasis and proliferation of cancer cells, and angiogenesis can be inhibited by inhibiting microRNA-382, and therefore it can be effectively used for treatment of cancer.

The pharmaceutical composition of the present invention may include a pharmaceutically-allowed carrier. Examples of the pharmaceutically-allowed carrier include a physiological saline solution, polyethylene glycol, ethanol, plant oil, and isopropyl myristate, but the present invention is not limited thereto.

Further, the present invention provides a method for treating cancer by administering a pharmaceutically effective amount of a composition for inhibiting angiogenesis including a microRNA-382 inhibitor to an individual. In the present invention, "individual" is understood to denote a subject which requires treatment of a disease, in particular, mammals such as humans or non-human primates, mice, rats, dogs, cats, horses, and cattle. Also, in the present invention, "a pharmaceutically effective amount" can differ depending on weight, age, sex, health, diet, administration time, administration method, excretion rate, and severity of a disease of a patient, and such a varied range and control thereof should be apparent to those skilled in the art.

A preferred dosage of the pharmaceutical composition of the present invention may differ depending on the condition and weight of a patient, degree of disease, drug form, administration pathway and duration, and can be appropriately selected by those skilled in the art. Nevertheless, the administration can preferably be conducted in an amount of 0.001 to 100 mg/weight kg per day, more preferably in an amount of 0.01 to 30 mg/weight kg per day. The administration may be conducted once a day, or divided into several times. An amount of the microRNA-382 inhibitor of the present invention may be 0.0001 to 10 wt %, preferably 0.001 to 1 wt %, relative to a total weight of the total composition.

The pharmaceutical composition of the present invention can be administered to mammals, such as rats, mice, livestock, and humans in various pathways. A method for administration is not particularly limited, and can be, for instance, oral, rectal, or intravenous, intramuscular, subcutaneous, intrauterine intradural, or intra cerbroventricular injection.

MODES OF THE INVENTION

Hereinafter, preferred embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

EXAMPLES

Example 1

Cultivation of Cells

Bovine aortic endothelial cells (BAECs) were introduced into a DMEM medium including 10% fetal bovine serum, and cultivated in an incubator comprising 5% carbon dioxide at 37° C. Gastric cancer cells of a human body were introduced into an RPMI-1640 medium including 10% fetal bovine serum, and cultivated in an incubator comprising 5% carbon dioxide at 37° C. After sufficient growth of the cells, they were cultivated in a 10 cm$^2$ culture plate for RNA (including microRNA) extraction and protein separation. When adherent cells were to be separated into two culture vessels, they were loosened from the culture vessel using trypsin-EDTA, centrifuged for 5 minutes at 1000 rpm, and moved to a new culture vessel in the same manner done for the adherent cells. When the hypoxia state was to be maintained, cultivation was performed in an incubator in which 1% $O_2$ concentration was maintained.

Example 2

Comparison of Expression Amount of microRNA-382 in Hypoxia State

The hypoxia state forms around cancer, and under such an environment, an expression amount of the various factors which control the mechanisms of cell proliferation and angiogenesis are subject to change. Among these, a comparison was made with microRNA showing a different expression amount when MKN1 cells, which are a gastric cancer cell strain, were under the hypoxia condition.

In particular, MKN1 cells were cultivated for 24 hours in 1% oxygen concentration. After 24 hours, the medium was quickly removed, and then the extracted RNA was treated to separate RNA. It was confirmed via microarray and real-time PCR that among the microRNA which shows a different expression amount under the hypoxia condition, microRNA-382 showed increased expression compared to the RNA separated from the MKN1 cells cultivated under the normal oxygen condition (refer to FIG. 1 and FIG. 2). A real-time PCR experiment method was performed as follows. All RNA of the MKN1 cells was extracted using a Purelink miRNA kit (Invitrogen) in accordance with the protocol of the manufacturer and a TRIzol reagent, and subsequently, complementary DNA (cDNA) was produced with 500 ng of the total RNA using a GenoExplorer™ miRNA First-Strand cDNA Core Kit (Genosensor). Real-time PCR was performed with SYBR Green PCR Master Mix (Applied Biosystems) and GenoExplorer™ miRNA qPCR Primer Sets (Genosensor) based on a Biosystems 7300 Real-Time PCR system. Mature microRNA was calculated at U6 RNA (internal control MKN1 cell).

FIG. 1 illustrates results showing an appearance of the expression of microRNA through microarray experiments when MKN1 cells, which are a gastric cancer cell strain, were cultivated under the hypoxia condition compared with that under the normal oxygen condition. As illustrated in FIG. 1, under the two conditions, the change was observed in the expression amount of many types of microRNA, and among them, the expression of microRNA-382 was increased under the hypoxia condition.

FIG. 2 illustrates the expression amount of microRNA-382 through the real-time PCR experiment in which MKN1 cells, which are a gastric cancer cell strain, were cultivated in accordance with time under the hypoxia condition. As illustrated in FIG. 2, it was confirmed via real-time PCR that microRNA-382 shows the highest expression at 24 hours under the hypoxia condition. In other words, it was confirmed that the expression of microRNA-382 is increased more under the hypoxia condition than under the normal oxygen condition, and the maximum expression of microRNA-382 was found at a cultivation time of 24 hours.

The above results suggest that microRNA-382 functions to control phenomena which appear in the hypoxia state formed in cancer cells.

Example 3

Confirmation of Proliferation Performance of Blood Vessel Endothelial Cells in Accordance with Expression of microRNA-382

Surrounding blood vessel endothelial cells are influenced by various growth factors secreted from cancer cells under a hypoxia micro-environment which is formed in the process of unbridled proliferation of cancer cells, and therefore proliferation may be accelerated.

Accordingly, the present inventors believed that microRNA-382, expression of which increases in cancer cells in the hypoxia state, may influence surrounding blood vessel endothelial cells, and therefore performed the following experiment.

In particular, MKN1 cells, which are a gastric cancer cell strain, were cultivated for one day in a medium that did not contain antibiotics, and then PNAs™ microRNA-382 inhibitor (PANAGENE) was transfected. After being cultivated for 20 hours in a normal oxygen state, they were moved to a 1% oxygen concentration and cultivated for 6 hours, 12 hours, and 24 hours. After each medium which was cultivated for a different time was extracted and concentrated, an experiment of treating blood vessel endothelial cells and observing proliferation performance was performed.

In order to observe proliferation performance of blood vessel endothelial cells, the blood vessel endothelial cells were cultivated for about 24 hours in a DMEM medium containing 10% FBS on a 48-well plate, then cultivated for 20 hours by changing the medium to one only containing 1% FBS, and then further cultivated for 24 hours by changing to the following conditioned medium. Each well was treated with 1 uCi of [$^3$H]-thymidine for 4 hours, and then washed three times with distilled water. After being fixed in methanol for 5 minutes at 4° C., it was washed three times with distilled water. After being treated with 5% trichloroacetic acid (TCA) for 10 minutes, it was washed with distilled water three times, and dissolved in 0.3 N sodium hydroxide, and then a radio-activity was measured using a liquid scintillation counter (Perkin Elmer) to confirm proliferation performance of the cells, results of which are illustrated in FIG. 3.

Figure 3:
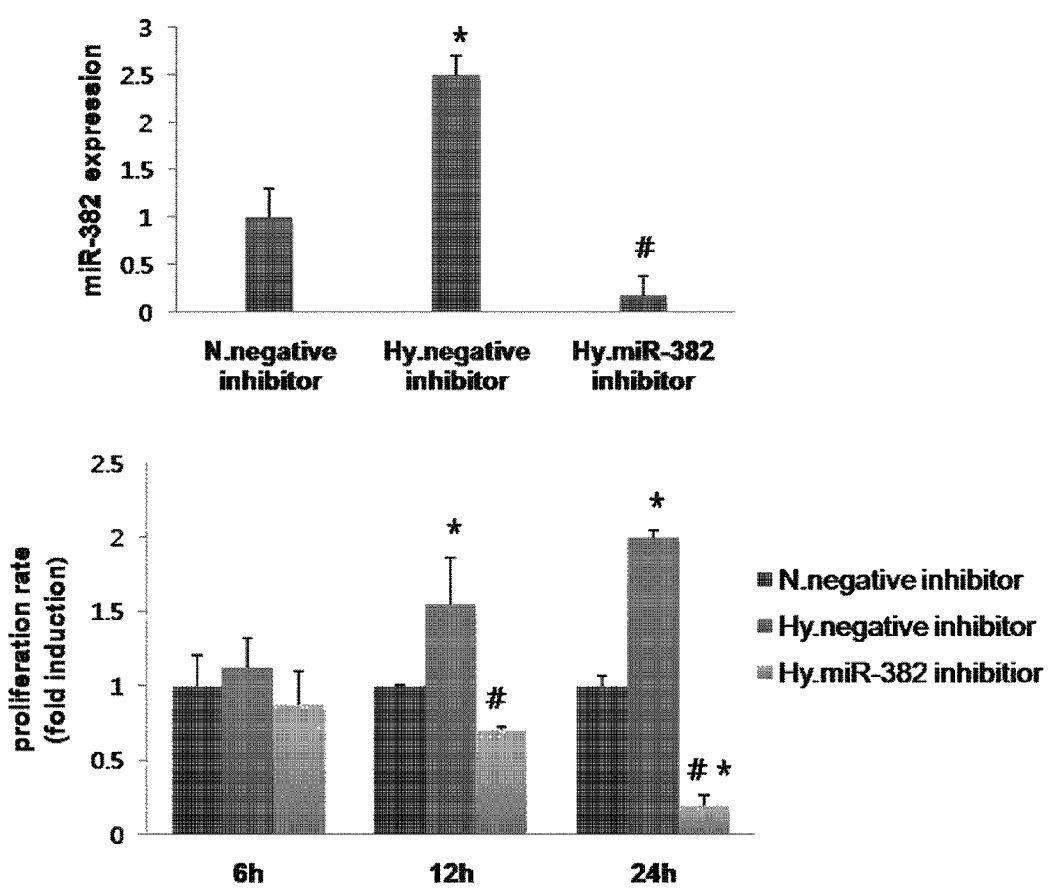
FIG. 3 illustrates results of inhibited proliferation performance of the cells when blood vessel endothelial cells were cultivated in the conditioned medium in which the increased expression of microRNA-382 under the hypoxia condition was decreased by treatment with an inhibitor.

As illustrated in FIG. 3, it was confirmed that the proliferation performance of blood vessel endothelial cells was decreased when the blood vessel endothelial cells were treated with the conditioned medium in which the increased expression of microRNA-382 under the hypoxia condition was decreased by treatment with an inhibitor.

From the above results, microRNA-382 can be expected to function to accelerate the proliferation performance of blood vessel endothelial cells, and in order to reconfirm this, the influence on the proliferation performance of blood vessel endothelial cells by over-expressing microRNA-382 under the normal oxygen condition was observed.

In particular, mature microRNA-382 which was cloned in a pENTR™/H1/T0 vector was transfected to MKN1 cells, which are a gastric cancer cell strain, to induce over-expression. After being cultivated for 24 hours, the medium was extracted and concentrated, treated in blood vessel endothelial cells, and the experiment to observe the proliferation performance was conducted, results of which are illustrated in FIG. 6.

As illustrated in FIG. 6, it was confirmed that an increase of expression of microRNA-382 increases the proliferation performance of blood vessel endothelial cells around cancer cells.

Example 4

Confirmation of Migration Performance of Blood Vessel Endothelial Cells in Accordance with Expression of microRNA-382

As in Example 3, an influence of microRNA-382, expression of which is increased in cancer cells in the hypoxia state, on a migration performance of blood vessel endothelial cells was observed in order to confirm an increase of migration performance of blood vessel endothelial cells under the influence of various surrounding growth factors secreted from cancer cells.

In particular, MKN1 cells, which are a gastric cancer cell strain, were cultivated for one day in a medium that did not contain antibiotics, and then, and then PNAs™ microRNA-382 inhibitor (PANAGENE) was transfected. After being cultivated for 20 hours in a normal oxygen state, it was moved to a 1% oxygen concentration and cultivated for 6 hours, 12 hours, and 24 hours. After each medium which was cultivated for a different time was extracted and concentrated, an experiment in which blood vessel endothelial cells were treated and migration performance was observed was performed.

In order to observe the migration performance of blood vessel endothelial cells, a 24-well transwell equipped with 8 μm porosity polycarbonate filters on which a type 1 collagen was coated and dried for 1 hour at room temperature was used. The extracted conditioned medium was inserted into the bottom of a chamber, a medium that did not contain serum together with the same number of cells was coated on the chamber and cultivated for 20 hours, and then a number of cells that passed through the layer was counted.

Figure 4:
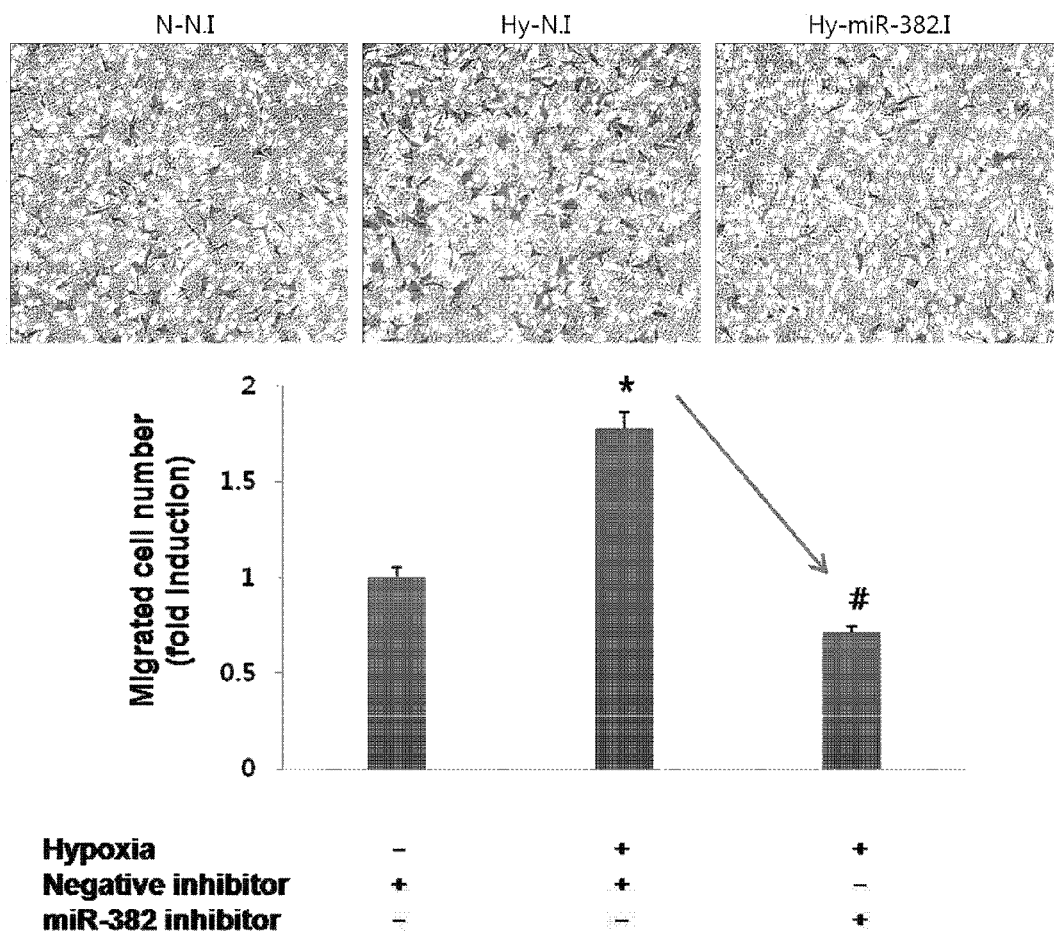
FIG. 4 illustrates results of inhibited migration performance of the cells when blood vessel endothelial cells were cultivated in the conditioned medium in which the increased expression of microRNA-382 under the hypoxia condition was decreased by treatment with an inhibitor.

Classification of the migrated cells was conducted by methanol fixation, 10 minute-staining with hematoxylin, 10 minute-staining with eosin, and removal of the un-migrated cells on the layer with a cotton swab, and then the stained cells were counted with a microscope, results of which are illustrated in FIG. 4.

As illustrated in FIG. 4, it was confirmed that the migration performance of blood vessel endothelial cells is decreased when the blood vessel endothelial cells are treated with the conditioned medium in which the increased expression of microRNA-382 in cancer cells under the hypoxia condition is decreased by treatment with an inhibitor.

From the above results, microRNA-382 was predicted to function to accelerate the migration performance of blood vessel endothelial cells, and in order to reconfirm this, the influence on the migration performance of blood vessel endothelial cells by over-expressing microRNA-382 under the normal oxygen condition was observed.

In particular, mature microRNA-382 which was cloned in a pENTR™/H1/T0 vector was transfected to MKN1 cells, which are a gastric cancer cell strain, to induce over-expression. After being cultivated for 24 hours, the medium was extracted and concentrated, treated in blood vessel endothelial cells, and the experiment to observe the migration performance was conducted, results of which are illustrated in FIG. 7.

As illustrated in FIG. 7, it was confirmed that an increase of expression of microRNA-382 increases the migration performance of blood vessel endothelial cells around cancer cells.

Example 5

Confirmation of Performance of Forming Blood Vessels of Blood Vessel Endothelial Cells in Accordance with Expression of microRNA-382

As in Example 3, the influence of microRNA-382, expression of which is increased in cancer cells in the hypoxia state, on a performance of forming blood vessel of blood vessel endothelial cell was observed in order to confirm an increase of the performance of forming blood vessel of blood vessel endothelial cell by the influence of surrounding various growth factors secreted from cancer cell In order to observe the performance of forming blood vessel of blood vessel endothelial cell, matrigel was coated in 48-well plate for 30 minutes at 37° C., blood vessel endothelial cells together with the conditioned medium extracted from cancer cell medium in which the microRNA-382, expression of which is increased in the hypoxia state, was decreased with an inhibitor were introduced into the well, and cultivated for 12 hours. Tube formation was observed with a microscope, results of which are illustrated in FIG. 5.

Figure 5:
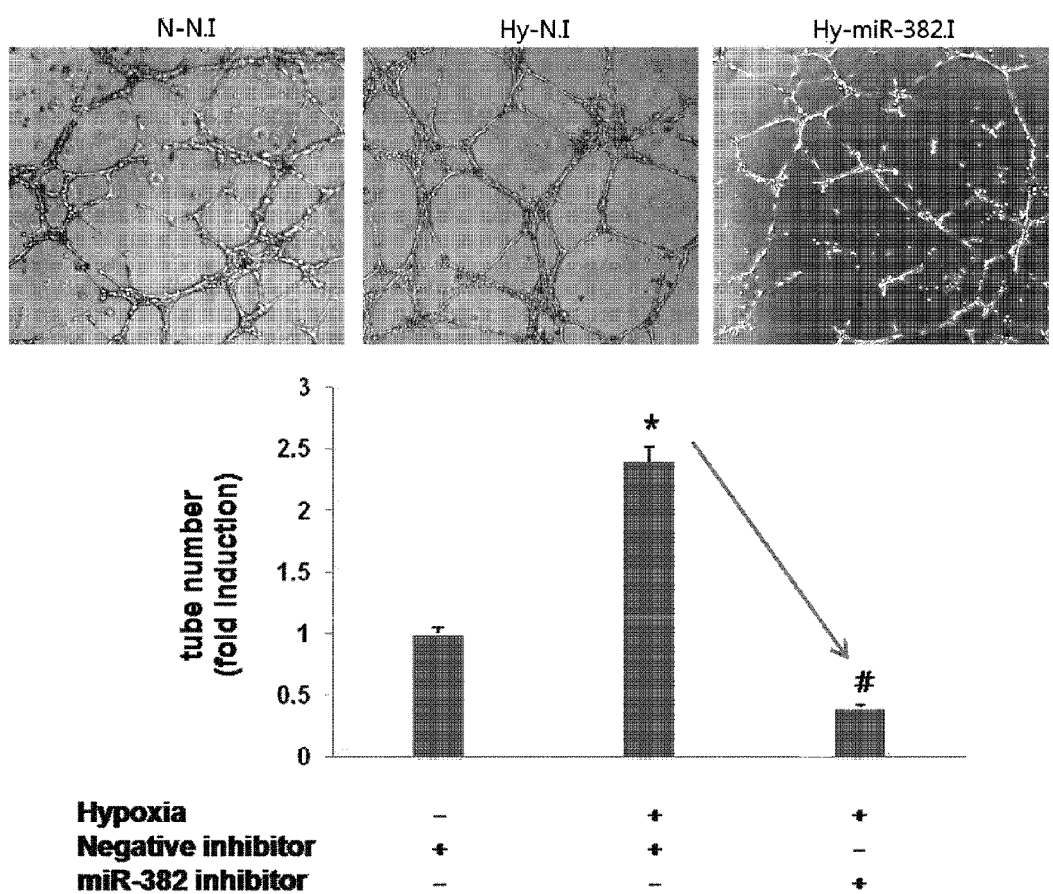
FIG. 5 illustrates results of inhibited performance of forming blood vessels of the cells when blood vessel endothelial cells were cultivated in the conditioned medium in which the increased expression of microRNA-382 under the hypoxia condition was decreased by treatment with an inhibitor.

As illustrated in FIG. 5, it was confirmed that the performance of forming blood vessels of blood vessel endothelial cells is decreased when the blood vessel endothelial cells are treated with the conditioned medium in which the increased expression of microRNA-382 in cancer cells in the hypoxia state is decreased by treatment with an inhibitor.

From the above results, microRNA-382 was predicted to function to accelerate the performance of forming blood vessels of blood vessel endothelial cells, and in order to reconfirm this, the influence on the performance of forming blood vessels of blood vessel endothelial cells by over-expressing microRNA-382 under the normal oxygen condition was observed.

After over-expressing microRNA-382 in the same manner, the performance of forming blood vessels of the cells which were introduced together with the extracted conditioned medium was observed, and it was confirmed that more tubes were formed, results of which are illustrated in FIG. 8.

As illustrated in FIG. 8, it was confirmed that an increase of expression of microRNA-382 increases the performance of forming blood vessels of blood vessel endothelial cells around cancer cells.

Example 6

Confirmation of Effect of microRNA-382 in Accelerating Angiogenesis In Vivo 6-1. Decreased Expression of PTEN Under Hypoxia Condition The present inventors conducted the following experiments in order to find a target gene of microRNA-382, expression of which is increased in cancer cells under the hypoxia condition.

In particular, among the target genes, PTEN was selected via Target Scan, miRanda and Sanger miRbase Target, which are programs which enable prediction of a binding site of a target gene of microRNA, and as a priority, the expression amount of PTEN in cancer cells under the hypoxia condition was confirmed.

Figure 9:
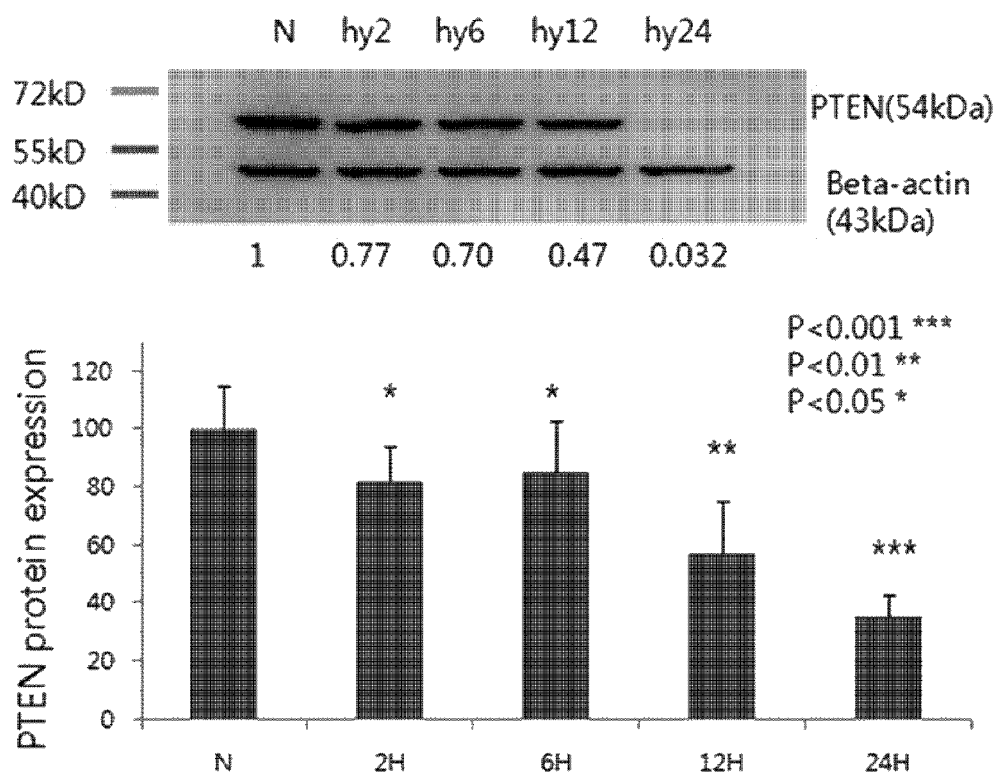
FIG. 9 illustrates results of confirming a decrease of an expression amount of PTEN in cancer cells under the hypoxia condition.

As a result, it was confirmed that the expression amount of PTEN is decreased in cancer cells under the hypoxia condition compared with those under the normal oxygen condition (refer to FIG. 9).

6-2. Confirmation of Binding of microRNA-382 and PTEN

From the above, the present inventors predicted that the target gene of microRNA-382 would be PTEN of which expression is decreased in cancer cells under the hypoxia condition, and therefore first found a site at which miR-130a and miR-495 bind to 3'-UTR of PTEN through the miRanda program. Further, it was confirmed that the site at which microRNA-382 binds to 3'-UTR of PTEN mRNA is preserved in many kinds (refer to FIG. 10).

In order to confirm direct binding of microRNA-382 to the binding site of PTEN as predicted above, the 3'-UTR portion of PTEN containing the binding site of microRNA-382 was cloned in a luciferase reporter vector to prepare a pGL3-luciferase-PTEN 3'-UTR-vector. Thereafter, the vector was transduced into cells, the cells to which the vector was transduced were treated with microRNA-382, and then a luciferase activity shown in the cells was measured.

Figure 11:
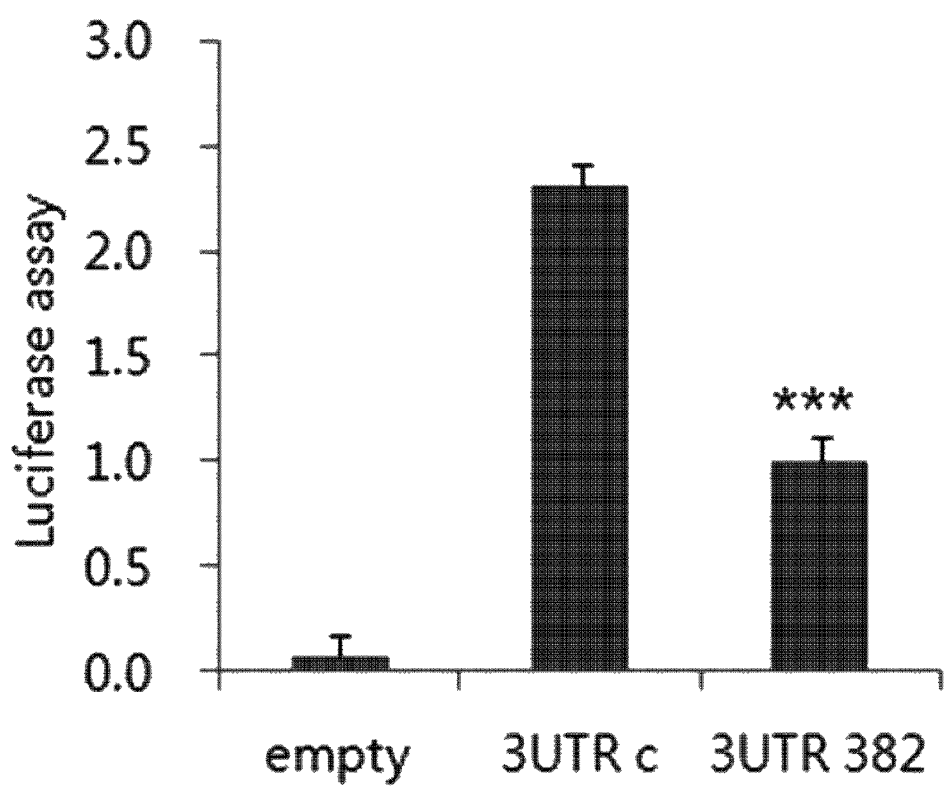
FIG. 11 illustrates a graph showing a measurement of activity of luciferase expressed in the cells after preparing a recombinant vector in which luciferase protein including 3'-UTR of PTEN was fused, and treating the cell strain to which the vector was transduced with microRNA-382 in order to confirm binding between microRNA-382 and 3'-UTR of PTEN.

As a result, it was confirmed that the luciferase activity is substantially decreased by the treatment with microRNA-382 in the cells to which the vector containing the 3'-UTR portion of PTEN is transduced (refer to FIG. 11). As such, it was revealed that a microRNA-382 directly binds to 3'-UTR of the target gene PTEN.

6-3. Decrease of expression of PTEN by miR-382

In order to confirm an influence of microRNA-382 on protein expression of PTEN, the present inventors confirmed the expression amount of PTEN protein by treating MKN1 cells, which are a gastric cancer cell strain, with miRNA mimic (MSY0000737) which can over-express microRNA, and an miRNA inhibitor (Qiagen miScript miRNAs) which can inhibit microRNA.

In particular, when the mimic of microRNA-382 was treated in cancer cells under the normal oxygen condition, the expression amount of PTEN protein was decreased in a concentration-dependent manner, and also, when the microRNA-382 inhibitor was treated in cancer cells under the hypoxia condition, the expression amount of PTEN protein was recovered in a concentration-dependent manner (refer to FIG. 12).

6-4. Confirmation of Effect of microRNA-382 in Accelerating Angiogenesis Through Chick Chorioallantoic Membrane (CAM) Assay The present inventors conducted a chick chorioallantoic membrane (CAM) assay to confirm the effect of microRNA-382 in accelerating angiogenesis in vivo.

In particular, the CAM assay was performed as follows.

A purchased fertilized egg was hatched in an incubator in which temperature and humidity were maintained at 37 to 38° C. and 90%, respectively, a hole was created with a knife at the terminal of the egg's narrow end, the hole was sealed, and the cultivation was conducted again with the hole facing down. Thereafter, a round window having a diameter of 2 to 3 cm was formed in the side on which the air sac of the egg was located (opposite to the hole for injection), only eggs which were confirmed to be fertilized were sealed with wide glass tape, and then cultivation was conducted again to induce production of CAM.

Then, for treatment with a microRNA mimic, a negatively stained group and a microRNA-382 mimic were transduced into cells under the normal oxygen condition, the conditioned medium obtained 24 hours later was concentrated 30-fold, a mixture was prepared by mixing with matrigel at a ratio of 1:1, and then treatment was performed on CAM.

Furthermore, for treatment with the microRNA inhibitor, a negatively stained group and a microRNA-382 inhibitor were transduced into cells, the hypoxia condition was applied 16 hours later, the conditioned medium was separated and concentrated 24 hours later, a mixture was prepared by mixing with matrigel at a ratio of 1:1, treatment was performed on CAM, and after 4 days, a close-up was taken with a camera.

As a result, it was confirmed that a number of branches of microvessels decreases in CAM in which the conditioned medium mixture including a microRNA-382 inhibitor is treated under the hypoxia condition compared with the instance in the hypoxia state, whereas a number of branches of microvessels increases in CAM in which the conditioned medium mixture including microRNA-382 is treated compared with the negatively stained group (refer to FIG. 13). From the above, it was revealed that microRNA-382 has an effect of accelerating angiogenesis in vivo as well.

6-5. Confirmation of Inhibiting Effect of microRNA-382 in Accelerating Angiogenesis Via PTEN Treatment The present inventors confirmed an inhibition of the effect of accelerating angiogenesis by treatment of PTEN protein, which is a target gene of microRNA-382.

In particular, a tube formation assay was performed to over-express PTEN protein using the conditioned medium obtained from the cells into which PTEN was transduced, and as a result, it was confirmed that the tube formation induced by microRNA-382 was inhibited by PTEN treatment (refer to FIG. 14).

In addition, it was confirmed via a CAM assay that angiogenesis increased by microRNA-382 is decreased by PTEN, and that angiogenesis is decreased by treating with a microRNA-382 inhibitor under the hypoxia condition compared with the hypoxia state (refer to FIG. 15).

Accordingly, it was revealed that the over-expression of PTEN inhibits the angiogenesis effect induced by microRNA-382.

The above embodiments of the present invention have been made merely for exemplary purposes, and it will be understood by those skilled in the art that they can be easily modified to other particular forms without departing from the technical idea or necessary characteristics. Therefore, the examples described above are merely exemplary and should not be understood to be restrictive.

The invention claimed is:

1. A method of treating a gastric cancer by promoting expression of PTEN in hypoxia conditions in a subject in need thereof, the method comprising administering to the subject a composition comprising a pharmaceutically effective amount of PNA (peptide nucleic acid) complementary to microRNA-382 as a microRNA-382 inhibitor.

* * * * *

SEQUENCE LISTING

```
<160> NUMBER OF SEQ ID NOS: 9

<210> SEQ ID NO 1
<211> LENGTH: 22
<212> TYPE: RNA
<213> ORGANISM: Artificial Sequence
<220> FEATURE:
<223> OTHER INFORMATION: chemically synthesized

<400> SEQUENCE: 1
gcuuaggugg ugcuuguuga ag                                              22

<210> SEQ ID NO 2
<211> LENGTH: 23
<212> TYPE: RNA
<213> ORGANISM: Artificial Sequence
<220> FEATURE:
<223> OTHER INFORMATION: chemically synthesized

<400> SEQUENCE: 2
uaccuacauc agucaacaac uua                                             23

<210> SEQ ID NO 3
<211> LENGTH: 28
<212> TYPE: RNA
<213> ORGANISM: Artificial Sequence
<220> FEATURE:
<223> OTHER INFORMATION: chemically synthesized

<400> SEQUENCE: 3
uaccuacauc agucaacaac uuacacuu                                        28

<210> SEQ ID NO 4
<211> LENGTH: 28
<212> TYPE: RNA
<213> ORGANISM: Artificial Sequence
<220> FEATURE:
<223> OTHER INFORMATION: chemically synthesized

<400> SEQUENCE: 4
uaccuacauc agucaacaac uuacacuu                                        28

<210> SEQ ID NO 5
```

```
<211> LENGTH: 28
<212> TYPE: RNA
<213> ORGANISM: Artificial Sequence
<220> FEATURE:
<223> OTHER INFORMATION: chemically synthesized

<400> SEQUENCE: 5
ucccuacauc agucaacaac uuacauuu                                            28

<210> SEQ ID NO 6
<211> LENGTH: 26
<212> TYPE: RNA
<213> ORGANISM: Artificial Sequence
<220> FEATURE:
<223> OTHER INFORMATION: chemically synthesized

<400> SEQUENCE: 6
uaccuacauc agucaacaac uuacac                                              26

<210> SEQ ID NO 7
<211> LENGTH: 28
<212> TYPE: RNA
<213> ORGANISM: Artificial Sequence
<220> FEATURE:
<223> OTHER INFORMATION: chemically synthesized

<400> SEQUENCE: 7
uaccuacauc agucaacaac uuacacuu                                            28

<210> SEQ ID NO 8
<211> LENGTH: 26
<212> TYPE: RNA
<213> ORGANISM: Artificial Sequence
<220> FEATURE:
<223> OTHER INFORMATION: chemically synthesized

<400> SEQUENCE: 8
uaccuacauc agucaacaac uuacac                                              26

<210> SEQ ID NO 9
<211> LENGTH: 27
<212> TYPE: RNA
<213> ORGANISM: Artificial Sequence
<220> FEATURE:
<223> OTHER INFORMATION: chemically synthesized

<400> SEQUENCE: 9
uaccuacauc agucaacaac uuacacu                                             27
```